United States Patent [19]
Cuif et al.

[11] Patent Number: 6,133,194
[45] Date of Patent: Oct. 17, 2000

[54] CERIUM OXIDES, ZIRCONIUM OXIDES, CE/ZR MIXED OXIDES AND CE/ZR SOLID SOLUTIONS HAVING IMPROVED THERMAL STABILITY AND OXYGEN STORAGE CAPACITY

[75] Inventors: Jean-Pierre Cuif, Princeton; Julie Lynn Shreeve Keyer; Steven Eric Deutsch, both of Plainsboro, all of N.J.

[73] Assignee: Rhodia Rare Earths Inc., Shelton, Conn.

[21] Appl. No.: 08/837,631

[22] Filed: Apr. 21, 1997

[51] Int. Cl.[7] .................................................. B01J 23/00
[52] U.S. Cl. ........................ 502/506; 502/508; 502/509; 502/510; 502/512; 502/513; 502/162; 502/167; 502/170; 502/304; 502/349
[58] Field of Search .................................. 502/506, 508, 502/509, 510, 512, 513

[56] References Cited

U.S. PATENT DOCUMENTS

| | | | |
|---|---|---|---|
| 1,070,138 | 8/1913 | Kast | 502/510 |
| 2,745,812 | 5/1956 | Ries, Jr. | 502/512 |
| 3,829,393 | 8/1974 | Sutherland et al. | 502/512 |
| 3,838,070 | 9/1974 | Thomas, Jr. | 502/510 |
| 3,862,055 | 1/1975 | Eurlings et al. | 502/508 |
| 4,102,821 | 7/1978 | Pessimisis | 502/512 |
| 4,172,809 | 10/1979 | Triki | 502/513 |
| 4,174,301 | 11/1979 | Choca et al. | 502/512 |
| 4,196,098 | 4/1980 | Hwang | 502/512 |
| 4,315,864 | 2/1982 | Bremer et al. | 502/512 |
| 4,315,874 | 2/1982 | Ushida et al. | 264/5 |
| 5,030,601 | 7/1991 | Michel et al. | 501/103 |
| 5,104,832 | 4/1992 | Michel et al. | 501/103 |
| 5,179,060 | 1/1993 | Subramanian et al. | 502/512 |
| 5,380,692 | 1/1995 | Nakatsuji et al. | 502/303 |
| 5,510,068 | 4/1996 | Parmentier | 264/117 |
| 5,532,198 | 7/1996 | Chopin et al. | 502/304 |
| 5,571,492 | 11/1996 | Yao et al. | 423/263 |
| 5,580,536 | 12/1996 | Yao et al. | 423/263 |
| 5,582,785 | 12/1996 | Yao et al. | 264/60 |
| 5,691,262 | 11/1997 | Hagemeyer et al. | 502/38 |
| 5,693,299 | 12/1997 | Chopin et al. | 423/213.2 |
| 5,712,218 | 1/1998 | Chopin et al. | 502/304 |
| 5,723,101 | 3/1998 | Cuif | 423/592 |
| 5,747,401 | 5/1998 | Cuif | 501/103 |
| 5,785,946 | 7/1998 | Pinnavaia et al. | 502/509 |
| 5,800,800 | 9/1998 | Pinnavaia et al. | 502/509 |

FOREIGN PATENT DOCUMENTS

| | | |
|---|---|---|
| 319 365 | 6/1989 | European Pat. Off. . |
| 395 912 | 11/1990 | European Pat. Off. . |
| 605 274 | 7/1994 | European Pat. Off. . |
| 629 438 | 12/1994 | European Pat. Off. . |
| 0778 071 | 6/1997 | European Pat. Off. . |
| 4437252 | 4/1996 | Germany . |
| 56-102939 | 8/1981 | Japan .................................. 502/510 |
| WO97/43214 | 11/1997 | WIPO . |
| WO98/16472 | 4/1998 | WIPO . |

OTHER PUBLICATIONS

Leitenburg, et al, A Novel and Simple Route to Catalysts with a High Oxygen Storage Capacity: the Direct Room–temperature Synthesis of CeO2–ZrO2 Solid Solutions, J. Chem Soc., Chem. Commun., 2181–2182 (1995).

Ozawa, et al, The Application of Ce–Zr Oxide Solid Solution to Oxygen Storage Promoters in Automotive Catalysts, J. of Alloys and Compounds, 193, 73–75 (1993).

Fornasiero, et al, "Rh–Loaded CeO2–ZrO2 Solid Solutions as Highly Efficient Oxygen Exchangers: Dependence of the Reduction Behavior and the Oxygen Storage Capacity on the Structural Properties", J. of Catalysis, 151, 168–177 (1995).

Duwez, et al, "Phase Relationships in the System Zirconia–Ceria", J. of the American Ceramic Society, vol. 33, No. 9, 274–283 (Sep. 1950).

Gogotsi, et al, "Mechanical Behaviour of Partially Stabilized Zirconia Crystals with Terbia and Ceria Additives", J. of the European Ceramic Society, 15, 1177–1184 (1995).

*Primary Examiner*—Mark L. Bell
*Assistant Examiner*—J. Pasterczyk
*Attorney, Agent, or Firm*—Katherine L. Carleton

[57] ABSTRACT

The production of cerium oxides, zirconium oxides, (Ce,Zr)$O_2$ mixed oxides and (Ce,Zr)$O_2$ solid solutions having improved particle size distribution, surface area, oxygen storage capacity and pore volume by the addition of an additive, such as anionic surfactants, nonionic surfactants, polyethylene glycols, carboxylic acids, and carboxylate salts, during the formation of the oxides or precursors thereof.

35 Claims, No Drawings

CERIUM OXIDES, ZIRCONIUM OXIDES, CE/ZR MIXED OXIDES AND CE/ZR SOLID SOLUTIONS HAVING IMPROVED THERMAL STABILITY AND OXYGEN STORAGE CAPACITY

BACKGROUND OF THE INVENTION

1. Field of the Invention

The present invention relates to the production of cerium oxides, zirconium oxides, cerium and zirconium mixed oxides or solid solutions (also hydroxides and carbonates) having improved thermal stability and oxygen storage capacity. The oxides, hydroxides or carbonates have a fine particle size distribution, very high surface area, oxygen storage capacity and release capacity, and are useful in many applications including catalytic converters, catalysis for the manufacture of styrene and catalysis for gas exhaust systems.

2. Background of the Invention

Oxides of cerium and zirconium, and particularly cerium and zirconium $(Ce,Zr)O_2$ mixed oxides and solid solutions, are used for many applications, including catalysts used in automotive catalytic converters and the like. Such oxides are typically formed by known precipitation techniques which involve the formation of precursors to, or the solid oxides in a liquid medium. When such oxides are to be used, for example, in catalytic converters, it is desirable to maximize the thermal stability of the compounds, as defined by the stability of the surface area of the material after aging at high temperature. It is also desirable to maximize the surface area of such mixed oxides in order to provide improved catalytic properties. In addition to $(Ce,Zr)O_2$ mixed oxides, the present invention also relates to cerium oxides, zirconium oxides, and mixtures thereof as well as cerium and zirconium $(Ce,Zr)O_2$ solid solutions (where substitution between cerium and zirconium in the network of the oxide, as opposed to being two different phases, which can be utilized as catalysts or as catalyst supports.

Increasingly stringent vehicle emissions standards make exhaust system operating conditions increasingly severe. The majority of modern gasoline fueled cars are equipped with so-called three-way catalysts to aftertreat their exhaust gases. The purpose of this system is to convert simultaneously carbon monoxide, hydrocarbons and nitrogen oxides by means of a precious metal based heterogeneous catalyst, whereby the engine's air-to-fuel ratio is controlled to obtain exhaust gas compositions that guarantee optimal conversions. Cerium-zirconium oxides are widely used in three-way catalysts for automotive exhaust treatment. Three-way automotive catalysts consist of precious metals (platinum, rhodium, etc.), promoters and supports such as γ-alumina. It is known that the addition of $CeO_2$ as a promoter results in an improvement of the dynamic performance for the removal of carbon monoxide (CO), nitrogen oxides ($NO_x$) and hydrocarbons (Hcs). However, the high temperature conditions of use in an automotive engine lead to significant degradation including surface area loss of supports, sintering of supported precious metals and deactivation of added cerium.

It is known that cerium oxides and zirconium oxides and cerium and zirconium mixed oxides can be used as a catalyst or as a catalyst support. It is also well known that a catalyst is generally more effective when the contact surface between the catalyst and the reagents is larger. For this purpose, it is necessary for the catalyst to be maintained in the most divided state possible, that is, that the solid particles which compose it be as small and individualized as possible. The fundamental role of the support, therefore, is to maintain the catalyst particles or crystallites in contact with the reagents, in the most divided state possible. During the extended use of a catalyst support, a decrease in the specific surface occurs due to the coalescence of the very fine micropores. During this coalescence, part of the catalyst is surrounded by the body of the support and can no longer be in contact with the reagents.

An object of the present invention is to provide a method for producing cerium oxides, zirconium oxides, cerium and zirconium $(Ce,Zr)O_2$ mixed oxides, and cerium and zirconium $(Ce,Zr)O_2$ solid solutions having improved thermal stability, surface area, porosity, and/or oxygen storage capacity. The method is preferred for use producing cerium oxides, $(Ce,Zr)O_2$ mixed oxides and $(Ce,Zr)O_2$ solid solutions, having improved thermal stability, surface area, porosity, and/or oxygen storage capacity.

Another object of the present invention is cerium oxides, zirconium oxides, $(Ce,Zr)O_2$ mixed oxides, and $(Ce,Zr)O_2$ solid solutions compositions having improved thermal stability surface area, porosity, and/or oxygen storage capacity. The oxides, mixed oxides and solid solutions produced can have very high surface areas, very high oxygen storage capacities and low particle size.

These and other objects of the present invention will be more readily apparent from the following description.

SUMMARY OF THE INVENTION

The present invention provides a novel way to improve the thermal stability, surface area, porosity, and/or oxygen storage capacity of cerium oxides, zirconium oxides, $(Ce,Zr)O_2$ mixed oxides, and $(Ce,Zr)O_2$ solid solutions obtained by processes such as precipitation, co-precipitation or thermohydrolysis, by introducing an additive, such as an anionic surfactant and/or nonionic surfactant, during the formation of the oxide or precursors thereof. By additionally washing or impregnating with an alkoxylated compound and/or additive, thermal stability, surface area, porosity, and/or oxygen storage capacity can be even further improved.

All ratios, proportions and percentages herein are by weight, unless otherwise specified.

DETAILED DESCRIPTION OF THE INVENTION

The thermal stability of inorganic compounds can be defined as the stability of the surface area when material is aged at high temperature. For many applications, particularly catalysis, high surface area and highly stable materials are required by end users. In accordance with the present invention, cerium and zirconium mixed oxides and solid solutions are produced having improved thermal stability, surface area, porosity, and/or oxygen storage capacity. The invention is also used producing cerium oxides, zirconium oxides and mixtures of cerium oxides and zirconium oxides having improved thermal stability, surface area, porosity, and/or oxygen storage capacity.

Many methods have been developed for the preparation of high surface area oxides, mixed oxides and solid solutions. They generally fall into four basic steps: synthesis of precursors, treatment of precursors before conversion to oxides, conversion of precursors to mixed oxides, and post treatment of mixed oxide material. The methods of synthesis to produce precursors for oxides include: aqueous precipitation or coprecipitation, organic coprecipitation, spray coprecipitation, and hydrothermal techniques. These are conventional methods known in the art. The method of the present invention is preferred for use with aqueous precipitation or coprecipitation and hydrothermal techniques. Most preferably, the method of the present invention is utilized with aqueous precipitation or coprecipitation.

Typically, processes which precipitate hydrous hydroxides in water are acid-base neutralizations or ion exchange reactions. This method typically involves thermal treatment to obtain high surface area oxides. The soluble salts which are frequently used include nitrates, carbonates, and halides which are typically "neutralized" by adding them to an aqueous ammonia solution, forming metal hydroxides. This is by far the most commonly used method for preparing precursors for oxide powders. Conventional processes, co-thermohydrolysis and aqueous coprecipitation, are generally described separately below:

Co-thermohydrolysis

The first stage of the co-thermohydrolysis process involves preparing a mixture, in aqueous medium, of at least a soluble cerium compound, preferably a salt, and or at least a soluble zirconium compound, preferably a salt. The mixture can be obtained either from solid compounds which are dissolved in water, or directly from aqueous solutions of these compounds, followed by mixing, in any order, of the defined solutions.

Of the water soluble cerium compounds, one example is Ce(IV) salts, such as nitrates including ceric ammonium nitrate, that are suitable for the present invention. Preferably, a cerium nitrate is used. The cerium (IV) salt solution can contain some cerium (III). However, it is preferred that the salt contains at least about 85% cerium (IV). An aqueous solution of cerium nitrate can be obtained by reacting nitric acid with a hydrated ceric oxide, prepared by a standard reaction of cerium (III) salt solution, carbonate for instance, with an ammonia solution in the presence of hydrogen peroxide, an oxidizing agent. Ceric nitrate solutions obtained by electrolytic oxidation of a cerous nitrate may also be used.

The aqueous solution of cerium (IV) salt can have some free acid, for instance a normality ranging from about 0.1 to about 4 N. In the present invention, it is possible to use either a solution containing some free acid or a pre-neutralized solution by addition of a base, such as an aqueous solution of ammonia or alkaline hydroxides, e.g., sodium, potassium, etc. Preferably an ammonia solution is used to reduce the free acidity. In this case, it is possible to define the neutralization rate (r) of the initial solution by the following equation:

$$r=(n_3-n_2)/n_1$$

wherein $n_1$ represents the total number of moles of Ce(IV) present in the solution after neutralization, $n_2$ represents the number of OH$^-$ ions effectively used to neutralize the initial free acidity from the Ce(IV) aqueous solution, and $n_3$ represents the total number of moles of OH$^-$ ions from the base added. When a neutralization step is used, excess base can be used in order to ensure the complete precipitation of the Ce(OH)$_4$ species. Preferably, r is lower than about 1, more preferably about 0.5.

The soluble zirconium salts used in the invention can be, for instance, zirconium sulfate, zirconyl nitrate or zirconyl chloride.

The amount of cerium and zirconium contained in the mixture substantially corresponds to the stoichiometric proportion required to obtain the final desired composition.

Once the mixture is obtained, it is then heated. This thermal treatment, called thermohydrolysis, is carried out at a preferred temperature of between about 80° C. and the critical temperature of the reacting medium, typically between about 80 and about 350° C., more preferably between about 90 and about 200° C.

The heating stage can be carried out under air or under an inert gas such as nitrogen. Any suitable reaction time can be used, usually between about 2 and about 24 hours. The thermal treatment can be performed under atmospheric pressure or under any higher pressure such as the saturated vapor pressure. When the temperature is higher than the reflux temperature of the reaction medium (usually higher than about 100° C.), for instance between about 150 and about 350° C., the reaction is performed in a closed reactor or autoclave. The pressure can be equal to the autogenic pressure and can be correlated to the chosen temperature. It is also possible to increase the pressure in the reactor. If required, some additional base can be added directly after the heating stage into the reaction medium in order to improve the yield of the reaction.

After the heating stage, a solid precipitate is recovered from the reactor and separated from the mother liquor by any process known by the state of art, for example filtration, settling or centrifugation.

The obtained precipitate optionally can be washed or impregnated with one or several alkoxylated compounds, as more fully described below. In one embodiment, the precipitate is then dried, under air conditions for instance, at a temperature ranging from about 80 to about 300° C., preferably from about 100 to about 150° C. The drying stage is preferably performed until substantially no more weight loss is observed. Conventional drying techniques such as spray drying can be utilized.

After the optional drying step, the recovered precipitate is then calcined. This allows the formation of a crystalline phase. Usually, the calcination is carried out at temperatures ranging from about 200 to about 1000° C. The calcination temperature is typically higher than about 300° C., and preferably ranges from about 400 to about 800° C.

In accordance with the present invention an additive, e.g., a nonionic surfactant and or an anionic surfactant, can be added to the salt solutions, the base, the reactor, and/or reaction media. The formation of the hydroxide (or other precursor) is to be in the presence of the additive preferably during the thermohydrolysis/heating stage or the optional additional neutralization stage/addition of base and most preferably during the optional neutralization stage.

In a preferred embodiment of the thermohydrolysis, the additive is added to the reactor during the neutralization stage.

Aqueous Coprecipitation

The aqueous precipitation or coprecipitation method comprises preparing a hydroxide (also referred to in the art as being an aqueous oxide) or carbonate or hydroxy carbonate by reacting a salt solution and a base in the presence of an additive, such as an anionic and/or nonionic surfactant, possibly in the presence of an oxidizing agent, and separating the precipitate obtained, possibly washing or impregnating it (preferably with an alkoxylated compound), and /or drying or calcining it.

The first stage of the co-precipitation process is the preparation of a mixture in an aqueous medium of at least a soluble cerium compound, preferably a salt, at least a soluble zirconium compound, preferably a salt, or both. The mixture can be obtained either from solid compounds which are dissolved in water, or directly from aqueous solutions of these compounds, followed by mixing, in any order, of the defined solutions. According to the present invention the reaction of the base and cerium and or zirconium compound (e.g., salt) solutions is done in the presence of an additive.

The cerium salt solution used can be any aqueous cerium salt solution, in the cerous and or ceric state, which is soluble in the conditions of preparation, in particular a cerous chloride or cerium nitrate solution in the cerous or ceric state or a mixture of the same. Suitable water soluble cerium compounds include cerium HI salts, and cerium nitrates or halides, e.g., chlorides, for instance. The zirconium salt solution used can be any aqueous zirconium salt solution which is soluble in the conditions of preparation. The soluble zirconium salts used in the invention can be nitrates, sulfates or halides, for instance, zirconium sulfate, zirconyl nitrate or zirconyl chloride. Zr (IV) salts can be utilized.

It is preferable to utilize a cerium or zirconium salt with a high degree of metal purity, preferably greater than about 90%, more preferably greater than about 95% and most preferably above about 99%. It is recognized that the Ce and/or Zr salts can comprise additional elements, such as Rare Earth elements, e.g., Pr or La, in varying amounts such as about 2%. The amount of cerium and/or zirconium contained in the mixture corresponds to the stoichiometric proportion required to obtain the final desired composition.

Optionally an oxidizing agent can be used. Among the oxidizing agents which are suitable are solutions of sodium, potassium or ammonium perchlorate, chlorate, hypochlorite, or persulfate, hydrogen peroxide or air, oxygen or ozone. An oxidizing agent, preferably hydrogen peroxide, can be added to the cerium/zirconium mixture or to the cerium or zirconium salt before mixing together. The amount of oxidizing agent in relation to the salts to be oxidized can vary within wide limits. It is generally greater than the stoichiometry and preferably corresponds to an excess.

The precipitation can be carried out by the reaction of the salt solution or solutions and a base solution. The base solution can be added to the cerium and or zirconium salt solution to precipitate out the hydroxides or carbonates or hydroxy carbonates (or the salt solutions can be added to the base solution). The base can be an ammonia solution or alkaline hydroxide solution, e.g., sodium, potassium, etc., or sodium, potassium or ammonia carbonate or bicarbonate solution. The base solution used can, in particular, be an aqueous solution of ammonia or of sodium or potassium hydroxide. An ammonia solution is preferably used. The normality of the base solution is not a critical factor in accordance with the invention; it can vary within wide limits. A preferred range is between about 1 and about 5 N, more preferably between about 2 and about 3 N. The quantity of the base solution utilized is determined such that the pH of the reaction medium is preferably greater than about 7. In the case of batch precipitation, the amount of base solution added is preferably at least the amount required to precipitate out $Ce(OH)_4$ and or $Zr(OH)_4$.

The precipitation is carried out on a batch or continuous basis. In the case of a continuous precipitation, the pH of the reaction is typically maintained between about 7 and about 11, preferably between about 7.5 and about 9.5. Generally, the mixing time in the reaction medium is not a critical factor and can vary within wide limits; generally between about 15 minutes and about 2 hours are selected. The residence time of the material in the reactor is typically at least about 15 minutes, preferably at least about 30 minutes. The reaction can be carried out at any suitable temperature such as room temperature.

After the reaction stage, a solid precipitate is recovered from the reactor and separated from the mother liquor by any process known in the state of art, for example filtration, settling or centrifugation. The precipitate can be separated by conventional solid/liquid separation techniques such as decantation, drying, filtration and/or centrifugation. The obtained precipitate can then be washed. Optionally, the obtained precipitate can then be washed or impregnated with one or several alkoxylated compounds, as described below.

The next stage of the process is calcination of the material, either with or without an intermediate drying step. This allows the formation of a crystalline solid solution phase. Usually, the calcination is carried out at temperatures ranging from about 200 to about 1000° C. Calcination temperatures of greater than about 300° C. are suitable, preferably ranging from about 350 to about 800° C.

As previously discussed, $(Ce, Zr)O_2$ mixed oxides can be prepared by various processes. Salts of Ce(III) and Zr(IV), nitrates for instance, can be mixed together and precipitated by adding a base such as sodium hydroxide or ammonia. Adequate precipitation conditions must be used to obtain the mixed oxide phase after calcination at high temperature. This process also requires the use of a base as a precipitating agent. In any case, the precipitate is separated from the mother liquor by any known techniques such as filtration, decantation or centrifugation. Once washed, the precipitate is either dried at about 120° C. and calcined at a minimum temperature of about 400° C. or directly calcined at the same temperature. The final preferred product is a pure mixed oxide with little or no organics since they are removed as a result of calcination.

Additives:

The use of an additive, e.g., ethoxylated alcohols or surfactants of anionic or nonionic nature, during co-precipitation, hydrothermolysis or the like, in order to improve the thermal stability, surface area, oxygen storage capacity, and or porosity of oxides or their precursors, preferably $(Ce, Zr)O_2$ mixed oxides, hydroxides and carbonates is provided. The process is suitable for the production of cerium oxides, zirconium oxides, $(Ce, Zr)O_2$ mixed oxides, $(Ce, Zr)O_2$ solid solutions, and the corresponding hydroxides or carbonates or hydroxy carbonates thereof, or mixtures thereof. The process is preferred for use in preparing cerium oxides, $(Ce, Zr)O_2$ mixed oxides, $(Ce, Zr)O_2$ solid solutions and mixtures thereof and most preferably for preparing $(Ce, Zr)O_2$ mixed oxides and $(Ce, Zr)O_2$ solid solutions.

In the current invention, an additive, such as a surfactant of anionic or nonionic nature, is present during the formation of the cerium, zirconium or (Ce,Zr) oxide(s) (mixed or solid solution) or precursors thereof, preferably during co-precipitation. The additive can generally be added to the: Metal salt solution, e.g., the Zr salt solution or Ce salt solution, a mixture of Ce and Zr salt solution, a base solution water, oxidizing agent or the reactor or reaction media. Optionally additional alkoxylated compounds or additives can also be added to the precipitate (generally in the form of a wet cake) obtained after liquid/solid separation or during the liquid/solid separation stage.

The additives can generally be described by the general formula:

$$R_1\text{—}((CH_2)_x\text{—}O)_n\text{—}R_2$$

where $R_1$ and $R_2$ represent a linear or non-linear alkyl, aryl, and/or alkylaryl group or H or OH or Cl or Br or I; n is a number between about 1 and about 100; and x is a number from about 1 to about 4. $R_1$ and $R_2$ can contain an alcohol group, a CO group, a S—C group etc. Preferred are compounds comprising alkoxy groups, particularly methoxy, ethoxy and propoxy groups which can generate an improvement of the thermal stability, surface area, porosity and or oxygen storage capacity.

Anionic and nonionic surfactants suitable for use herein are described in *Handbook of Surfactants,* M. R. Porter, Blackie & Son Ltd., Glasgow, 1991, pp. 54 to 115, which is incorporated herein by reference. The terms "anionic surfactant", "nonionic surfactant" or "additive" as used herein encompass mixtures of surfactants as well as mixtures of other types of additives. The additive of the present invention can advantageously be provided in the form of an aqueous solution having a relatively minor amount of the additive, e.g., anionic or nonionic surfactant. The additive preferably comprises less than about 50 wt. % of the aqueous solution, and more preferably comprises from about 0.1% to about 30 wt. % of an aqueous solution. A preferred commercially available additive suitable for use is sold by Rhône-Poulenc Inc. under the tradename IGEPAL® nonionic ethoxylates.

Anionic surfactants suitable for use include: carboxylates, phosphates, sulfates and sulfonates.

Suitable carboxylates have the general formula R—CH$_2$C(O)O$^-$ and include:

a) ethoxycarboxylates of the formula: R—O(CH$_2$CH$_2$O)$_x$CH$_2$COO$^-$, which includes ether carboxylates of the formula:

$$R-O-(CH_2CH_2O)_n CH_2 \underset{\underset{O}{\|}}{C}-O^-M^+$$

wherein R is an alkyl or alkylaryl group, M$^+$ can be ammonium, potassium, sodium or trithanolamine, and n$^2$ can be from about 1 to about 13;

b) ester carboxylates of the formula: R$_1$—CH$_2$—C[C(O)O](OH)(—R$_2$); and c) sarcosinates of the formula: R—C(O)N(CH$_3$)CH$_2$COO$^-$ Phosphates have the general formula: R$_2$PO$_4$ and include:

a) phosphate esters of the formulae (HO)(OR)P(O)$_2^-$ and O)$_2$P(O)$_2^-$ $$RO(CH_2CH_2O)_n\underset{MO}{\overset{O}{\underset{\|}{P}}}OM \qquad \underset{RO(CH_2CH_2O)_n}{RO(CH_2CH_2O)_n}\overset{O}{\underset{\|}{P}}OM$$

where R is an alkyl or alkyaryl group, n is moles of ethylene oxide (and/or propylene oxide) and M is hydrogen, sodium, potassium, or other counterion.

Suitable sulfates have the general formula: ROSO$_3^-$ and include:

a) alcohol sulfates;
b) alcohol ether sulfates; and
c) sulfated alkanolamide ethoxylate.

Suitable sulfonates have the general formula: RSO$_3^-$ and include:

a) sulphosuccinates;
b) taurates;
c) isethionates;

$$R-C(O)CH_2CH_2SO_3^-$$

d) alkyl benzene sulfonates;
e) fatty acid and diester sulfonates;
f) α-sulfo fatty acid esters;

g) alkyl naphthalene sulfonates;
h) formaldehyde naphthalene sulfonates;
i) olefin sulfonates; and
j) petroleum sulphonates.

Nonionic surfactants suitable for use include: acetylenic surfactants; alcohol ethoxylates; alkanolamides; amine oxides; ethoxylated alkanolamides; ethoxylated long chain amines; ethylene oxide/propylene oxide (EO/PO) co-polymers; sorbitan derivatives; ethylene glycol, propylene glycol, glycerol and polyglyceryl esters plus their ethoxylated derivatives; allyl amines; alkyl imidazolines; ethoxylated oils and fats; and alkyl phenol ethoxylates (ethoxylated alkyl phenols).

Preferred nonionic surfactants include the ethoxylated alkyl phenols supplied by Rhône-Poulenc Inc. under the trademark "IGEPAL"® and including:

IGEPAL® CA 720: octyl phenol of about 12 EO such as represented by the formula:

$$C_8H_{17}-\langle\text{phenyl}\rangle-O-(CH_2CH_2O)_{12}H$$

IGEPAL® CO 630: nonylphenol ethoxylated polyethylene glycol or nonophenol of about 9 EO such as represented by the formula:

$$C_9H_{19}-\langle\text{phenyl}\rangle-O-(CH_2CH_2O)_9H$$

Additionally, IGEPAL® CO 630 is well characterized in *Physio-Chemical Properties of Selected Anionic, Cationic and Nonionic Surfactants,* N. M. Van Os et al., Amsterdam, 1993, pp. 312–316, 318 and 342 which is incorporated herein by reference.

Also useful are IGEPAL® RC nonionic surfactants and IGEPAL® DN nonionic surfactants (dodecyl phenol+5 to 14 EO) which are supplied by Rhône-Poulenc Inc.

Also useful are tristyrylphenol ethoxylates.

Other preferred nonionics are glycol monoethers supplied by Dow Chemical under the tradename "DOWANOL" nonionic surfactant and including:

DOWANOL: ethylene glycol n-butyl ether $$Bu-O-CH_2CH_2-OH$$

DOWANOL nonionic surfactant DB: diethylene glycol n-butyl ether $$Bu-O-CH_2CH_2-O-CH_2CH_2-OH$$

DOWANOL nonionic surfactant TBH: triethylene glycol n-butyl ether and higher $$Bu-O-CH_2CH_2-O-CH_2CH_2-O-CH_2CH_2-OH$$

Other preferred nonionic surfactants for use include the alkanolamides which are the simplest members of the polyoxyethylene alkylamide family. Their formula can be either $R_1C(O)NH(CH_2CH_2OH)$ or $R_1C(O)N(CH_2CH_2OH)_2$ where $R_1$ represents a linear or non-linear alkyl group comprising from about 1 to about 50° C. or H. Monoalcoholamides are generally solids while dialcoholamides are generally liquids. Both types can be used, preferably with coprecipitation. They include those sold by Rhone-Poulenc Inc. under the trademark "ALKAMIDE"® and including:

ALKAMIDE LE®:

ALKAMIDE® L203:

Other preferred nonionic surfactants include ethoxylated amines such as those sold under the trademark "RHO-DAMEEN" by Rhone-Poulenc Inc. and including:

RHODAMEEN 532 SPB: Tallowamines, ethoxylated:

Other preferred nonionic surfactants include amine oxides including those supplied by Rhone-Poulenc Inc. under the trademark "RHODAMOX"® and including:

RHODAMOX LO: lauryl dimethylamine oxide:

Other additives are the polyethylene glycols. Polyethylene glycols include:

Other additives suitable for use are carboxylic acids, both mono and dicarboxylic acids. The general formula for a carboxylic acid can be represented as:

Suitable carboxylic acids are listed:

| TRIVIAL NAME | STRUCTURE | GENEVA NAME |
|---|---|---|
| MONOCARBOXYLIC | | |
| Formic | $H-CO_2H$ | Methanoic acid |
| Acetic | $CH_3-CO_2H$ | Ethanoic acid |
| Propionic | $CH_3-CH_2-CO_2H$ | Propanic acid |
| Butyric | $CH_3-CH_2-_2CO_2H$ | Butanoic acid |
| Isobutric | $CH_3-CH(CH_3)-CO_2H$ | 2-Methylpropanoic acid |
| Valeric | $CH_3-CH_2-_2CO_2H$ | Pentanoic acid |
| Caproic | $CH_3-CH_2-_4CO_2H$ | Hexanoic acid |
| Caprylic | $CH_3-CH_2-_6CO_2H$ | Octanoic acid |
| Capric | $CH_3-CH_2-_8CO_2H$ | Decanoic acid |
| Lauric | $CH_3-CH_2-_{10}CO_2H$ | Dodecanoic acid |
| Myristic | $CH_3-CH_2-_{12}CO_2H$ | Tetradecanoic acid |
| Palmitic | $CH_3-CH_2-_{14}CO_2H$ | Hexadecanoic acid |
| DICARBOXYLIC | | |
| Oxalic | $HO_2C-CO_2H$ | Ethanedioic acid |
| Malonic | $HO_2C-CH_2-CO_2H$ | Propanedioic acid |
| Succinic | $HO_2C-CH_2-_2CO_2H$ | Butanedioic acid |
| Glutaric | $HO_2C-CH_2-_3CO_2H$ | Pentanedioic acid |
| Adipic | $HO_2C-CH_2-_4CO_2H$ | Hexanedioic acid |
| Pimelic | $HO_2C-CH_2-_5CO_2H$ | Heptanedioic acid |
| Suberic | $HO_2C-CH_2-_6CO_2H$ | Octanedioic acid |
| Azelaic | $HO_2C-CH_2-_7CO_2H$ | Nonanedioic acid |
| Sebacic | $HO_2C-CH_2-_8CO_2H$ | Decanedioic acid |

Carboxylate salts can also be utilized as additives.

As described previously the additives are to be present during the formation of the cerium hydroxide, oxide, hydroxy carbonate and/or carbonate, zirconium hydroxide, oxide, hydroxy carbonate and/or carbonate, cerium/zirconium (Ce,Zr) hydroxide, oxide (mixed or solid solution, i.e., one phase), hydroxy carbonate and/or carbonate. (For the addition of the nonionic ethoxylates and (e.g., IGEPAL® surfactants) and the polyethylene glycols, it is preferred that the ethoxylates be added to either the metal (e.g., Ce,Zr) salt solution or solutions, preferably a cerium nitrate and/or zirconium nitrate aqueous solution, and/or the base solution, preferably an ammonia solution. Most preferably, the ethoxylates are added to the nitrate solutions and the ammonia solutions prior to reaction. For the amide surfactants (e.g., ALKAMIDE® surfactants), it is preferred to add to the metal (e.g., Ce,Zr) salt solution or solutions, preferably a cerium nitrate and/or zirconium nitrate solution, and/or water and/or the oxidizing agent and mixtures thereof.

For the addition of the carboxylic acid(s), addition to the base solution is preferred, preferably addition to an ammonia solution.

The determination of an effective amount of addition for the additives is within the skill of an artisan. Generally, the additives are added (based on the weight percent of the reaction media and reagents) of from about 1% to about 35%, preferably from about 2% to about 30% and most preferably from about 3% to about 30%. For the ethoxylated additives, it is generally preferred to utilize from about 2.5% to about 35% and preferably from about 10% to about 25%. For the amide additives, it is generally preferred to utilize from about 1% to about 10% and preferably from about 2% to about 5%. An excess of additive can be utilized without detrimentally effecting the benefits of addition.

Optional Washing/Impregnation

Most industrial processes which include the precipitation or the creation of a solid in a liquid medium involve a solid/liquid separation state. Filtration, decantation or centrifugation are among the known techniques used for this purpose. After the solid/liquid separation is completed, the so-called wet cake comprises precipitated particles and remaining mother liquor. In most of the processes, the mother liquor contains some salts that can contaminate the oxides generated during the next calcination operation. To reduce the amount of contaminants, washing is needed during and/or after the solid/liquid separation. In cases where the salts used as raw materials to make the precipitation are soluble in water, washing is typically carried out with water. The volume and temperature of water used for washing determine the purity of the material and its thermal stability as well.

The process of the present invention optionally includes the use of alkoxylated compounds having greater than 2 carbon atoms during the washing or impregnating stage in order to improve the thermal stability of cerium and or zirconium oxides and preferably $(Ce,Zr)O_2$ mixed oxides and solid solutions. The alkoxylated compounds suitable for use herein have greater than 2 carbon atoms.

In the scope of the present invention, the solid oxide material is separated from liquid by filtration or any other suitable method. In a preferred embodiment, the solid, otherwise called wet cake, is washed during a first stage with water to remove the water-soluble salts, nitrates for instance if nitrate solutions are the raw materials for the reaction. In a second stage of the preferred embodiment, the wet cake is washed or impregnated with a solution containing alkoxylated compounds such as ethoxylated alcohols, organic compounds or ethoxylated polymers such as PEG. Once washed or impregnated, the wet cake is either dried and calcined or directly calcined. The final product is a pure mixed oxide having substantially no organics since they are removed during calcination.

The alkoxylated compounds of the present invention can be defined by the general formula:

wherein $R_1$ and $R_2$ represent linear or non-linear alkyl, aryl and/or alkylaryl groups or H or OH or Cl or Br or I; n is a number from 1 to 100; and x is a number from 1 to 4. $R_1$ and $R_2$ can contain an alcohol group. Of the alkyl groups, methoxy, ethoxy and propoxy groups are preferred in order to generate an improvement in the thermal stability of the $(Ce,Zr)O_2$ mixed oxides and solid solutions.

The alkoxylated compound can be of the formula:

wherein $R_1$ is selected from the group consisting of linear and nonlinear alkyl groups having from 1 to 20 carbons and fatty hydrocarbon residues having from 8 to 20 carbons, n is from 1 to 100, and x is from 1 to 4. Preferably, n is from 12 to 40 and x is from 1 to 3. More preferably, x is 2.

The alkoxylated compound can be of the formula:

$H(OCH_2)_nOH$ or $H(OEt)_nOH$, wherein the average of n is from 1 to 100.

Examples of suitable alkoxylated compounds can be of the formulae:

wherein the average of x is 9 or from 4 to 15;

wherein the average of x is 12;

Commercially available alkoxylated compounds suitable for use are sold by Rhône-Poulenc Inc. under the trade names: IGEPAL® CO 630, IGEPAL® CA 720, ALKAMIDE® LE, and ALKAMIDE® L203.

The alkoxylated compound can alternatively be of the formula:

wherein $R_2$ and $R_3$ are the same or different and are independently selected from the group consisting of hydrogen and linear and nonlinear alkyl groups having from 1 to 20 carbons, n is from 1 to 100, and x is from 1 to 4. Preferably, n is from 12 to 40 and x is from 1 to 3. More preferably, x is 2.

The alkoxylated compound can further be of the formula:

wherein $R_4$ is selected from the group consisting of linear and nonlinear alkyl groups having from 1 to 20 carbons, n is from 1 to 100, and x is from 1 to 4. Preferably, n is from 12 to 40 and x is from 1 to 3. More preferably, n is 3, and x is 2.

The alkoxylated compound can further be of the formula:

wherein $R_5$ is selected from the group consisting of linear and nonlinear alkyl groups having from 1 to 20 carbons, n is from 1 to 100, and x is from 1 to 4. Preferably, n is from 4 to 40 and x is from 1 to 3. More preferably, x is 2.

The alkoxylated compound can also be of the formula:

wherein $R_6$ is selected from the group consisting of linear and nonlinear alkyl groups having from 1 to 20 carbons, n is from 1 to 100, and m is from 0 to 300 preferably 0 to 100. Preferably, n is from 12 to 40 and m is from 1 to 40.

The alkoxylated compound can alternatively be of the formula:

wherein o is from 0 to 300, m is from 0 to 300, and p is from 0 to 300.

The alkoxylated compound can further be of the formula:

wherein $R_7$ is selected from the group consisting of linear and nonlinear alkyl groups having from 1 to 20 carbons, n is from 1 to 100, and x is from 1 to 4. Preferably, n is from 4 to 40 and x is from 1 to 3. More preferably, x is 2.

The alkoxylated compound can further be of the formula:

wherein m is from 0 to 300, p is from 0 to 300, and q is from 0 to 300 and having an average molecular weight of from about 40 to about 8,000.

The alkoxylated compound can comprise, or be derived from, compounds as listed below:

Polyoxyalkylenated (polyethoxyethylenated, polyoxypropylenated, polyoxybutylenated) alkylphenols in which the alkyl substituent is $C_6$–$C_{12}$ and containing from 5 to 25 oxyalkylene units; examples include TRITONS X-45, X-114, X-100 and X-102, polyoxyalkenylated alkylphenols marketed by Rohm & Haas Co.;

glucosamide, glucamide, and glycerolamide;

polyoxyalkylenated $C_6$–$C_{22}$ aliphatic alcohols containing from 1 to 25 oxyalkylene (oxyethylene, oxypropylene) units; examples include TERGITOL® 15-S-9 and TERGITOL® 24-L-6 alcohols, marketed by Union Carbide Corp.; NEODOL®B 45-9, NEODOL® 23-65, NEODOL® 45-7 and NEODOL® 45-4 alcohols, marketed by Shell Chemical Co.; and KYRO(® KOB alcohols marketed by the Procter & Gamble Co.;

the products resulting from the condensation of ethylene oxide, the compound resulting from the condensation of propylene oxide with propylene glycol, such as the PLURONICS products marketed by BASF;

the products resulting from the condensation of ethylene oxide, the compound resulting from the condensation of propylene oxide with ethylenediamine, such as the TETRONICS products marketed by BASF;

amine oxides such as ($C_{10}$–$C_{18}$ alkyl) dimethylamine oxides and ($C_6$–$C_{22}$ alkoxy) ethyldihydroxyethylamine oxides;

the alkylpolyglycosides described in U.S. Pat. No. 4,565,647;

$C_6$–$C_{20}$ fatty acid amides;

$C_6$–$C_{20}$ alkamides, preferably utilized at low concentrations;

ethoxylated fatty acids; and ethoxylated amines.

The alkoxylated compound of the present invention can advantageously be provided in the form of an aqueous solution having a relatively minor amount of the alkoxylated compound. The alkoxylated compound preferably comprises less than about 50 wt. % of the aqueous solution, and more preferably comprises from about 0.1 to about 30 wt. % of the aqueous solution. A preferred commercially available compound suitable for use is sold by Rhône-Poulenc Inc. under the tradename IGEPAL® CA 720 surfactant.

The alkoxylated compounds can also be utilized as additives as described above. Conversely, the additives as described above can be utilized in the washing or impregnation of carbonates, hydroxides or oxides of cerium, zirconium, Ce/Zr mixed or solid solutions. Preferred additives for use are carboxylic acids, carboxylate salts and anionic surfactants. An embodiment of the present invention is the washing or impregnation utilizing the additives, preferably additives which are not ethoxylated. Impregnation is addition of the alkoxylated compound and/or additive, preferably with mixing, to the oxide, hydroxide or carbonate, preferably in the form of a wet cake, followed by calcining. The preferred impregnation surfactant is an ethoxylated alkylphenol. The alkoxyleted compound or additive is usually added at an amount equal to the weight of total oxide, hydroxide or carbonate in the wet cake. The material is then calcined at a temperature high enough to ensure removal of carbonaceous remnants from the oxide, hydroxide or carbonate.

For example instead of being present during the formation, a carboxylic acid, such as lauric acid, can be utilized in the washing or impregnation of a hydroxide, oxide or carbonate of cerium, zirconium, cerium/zirconium mixed or solid solutions. A preferred embodiment would be a carboxylic acid dissolved in aqueous ammonia or the like for washing or impregnation. The preferred mole ratio range for ammonia ($NH_3$) to carboxylic acid is about 0 to about 4, preferably about 1.5 to about 3.5.

Oxides and Solid Solutions

Mixed oxides or solid solutions produced utilizing the additives typically have a weight ratio of $CeO_2$ to $ZrO_2$ of from about 5:95 to about 95:5, preferably from about 95:5 to about 40:60. The mixed oxides and solid solutions, preferably being cerium rich, have a very high surface area, for example, greater than about 25 $m^2/g$, preferably greater than about 30 $m^2/g$, and more preferably greater than about 35 $m^2/g$ after calcination at about 900° C. for about 6 hours. "Cerium rich" refers to cerium zirconium mixed oxides having a formula of $(Ce_xZr_{1-x})O_2$ where x is greater than or equal to about 0.5. The mixed oxides and solid solutions, preferably being cerium rich, also have a very high oxygen storage capacity, for example, greater than about 2, preferably greater than about 2.6 ml $O_2/g$ after calcination at about 500° C. for about 2 hours.

The surface area of the oxides and mixed oxides produced in accordance with the present invention is designated as B.E.T. determined by nitrogen adsorption according to the standard procedure ASTM D 3663-78 established from the method by BRUNAUER-EMMET-TELLER described in *Journal of the American Chemical Society*, 60, 309 (1938). Thermal stability is designated as the surface area of any powdery inorganic material after aging at a given temperature for a certain time. In the current invention, 10 g of material are calcined in a muffle furnace for about 6 hours at about 900° C. After this aging stage, the surface area of the material was measured by the method previously described.

Oxides produced with the addition of additives as described herein provide for cerium oxides, zirconium oxides, cerium/zirconium mixed oxides or cerium/zirconium solid solutions having a total pore volumes greater than about 0.5 ml/g after calcination at about 500° C. for about 2 hours, preferably from about 0.5 to about 1 ml/g after calcination at about 500° C. for about 2 hours and most preferably greater than about 0.6 or 0.8 after calcination at about 500° C. for about 2 hours.

The following examples illustrate various aspects of the invention and are not intended to limit the scope thereof.

EXAMPLE 1

Using a co-precipitation method and a nitrate solution of cerium and zirconium, a mixed oxide composition of: $CeO_2$=80 wt % $ZrO_2$=20 wt % is prepared. By reacting the various salts in stoichiometric amounts and adding ammonia to the mixed nitrates to reach a pH of about 9, the mixed hydroxides, corresponding to about 30 g of dried rare earth oxides (REO) are precipitated out from the solution and filtered on a Büchner filter. The cake is washed with about 12.5 ml of deionized water per gram of oxide, then calcined for about 2 hours at about 500° C. The thermal stability of the product is evaluated after calcination under air in a muffle furnace at about 900° C. for about 6 hours. The surface area is measured at about 22 $m^2/g$ by the B.E.T. method (Micromeretics Gemini 2360).

EXAMPLE 2

The experiment described in Example 1 is repeated. However, an IGEPAL® CA 720 (Octyl Phenol containing 12 EO groups) surfactant is added during the preparation of the Ce/Zr mixed oxide. The ratio moles of surfactant to moles of total metal is about 1.11. The surfactant is added into the nitrate metal solution and the ammonia solution. The concentration of pure surfactant is about 20% in the nitrate solution and about 30% in the ammonia solution. The obtained wet cake is washed with about 12.5 ml of deionized water per g of oxide, and calcined as in Example 1. The surface area measured after calcination under air at about 900° C. for about 6 hours is about 33 $m^2/g$. The increase is about 47.5% compared to the product made without surfactant.

EXAMPLE 3

The conditions used in Example 1 are utilized again. However, the mixed oxide is prepared in the presence of an Alkamide LE® surfactant, which is an alkanolamide with a $C_{11}$ chain. The amount of surfactant added is 0.13 moles per mole of metals. All the alkanolamide is added to the mixed nitrate solution. The surface area measured after calcination under air at about 900° C. for about 6 hours is about 35 $m^2/g$. This example further demonstrates the effect a small amount of surfactant has on the improvement of thermal stability.

EXAMPLE 4

In this example a Zr rich mixed oxide is prepared. The stoichiometric amounts of Ce nitrate solution and Zr nitrate solution are mixed to obtain a product with the following composition: 80 wt % $ZrO_2$ and 20 wt % $CeO_2$. The mixed oxide is precipitated using the procedure described in Example 1. The surface area after calcination under air at about 900° C. for about 6 hours is about 32 $m^2/g$.

EXAMPLE 5

The conditions used in Example 4 are utilized. In this case however, the mixed oxides are precipitated in the presence of IGEPAL® CA 720 surfactant (Phenol Aromatic Ethoxylated—nonionic). The amount of surfactant used is 0.96 moles per mole of metal. IGEPAL® CA 720 surfactant is added to both the ammonia solution (concentration of surfactant is about 20 wt %) and to the nitrate solution (concentration of surfactant is about 22 wt %). The thermal stability after calcination under air at about 900° C. for about 6 hours is about 38 $m^2/g$, indicated an improvement of approximately 19% compared to the product made without surfactant.

EXAMPLE 6

Oxygen Storage Capacity (OSC) is measured on the sample obtained in Example 1. OSC is obtained using alternate pulses of CO and $O_2$ in He passed through the mixed oxide bed at about 400° C. in order to simulate rich and lean conditions in an engine. CO is diluted to about 5% in He and $O_2$ to about 2.5% in the same inert gas. The continuous flow rate of He is about $10.1.h^{-1}$ and the catalyst volume is about 0.1 $cm^3$. $O_2$, CO and $CO_2$ are measured using gas chromatography. OSC is evaluated from the alternate pulses. The result is about 1.6 ml $O_2$/g of mixed oxide (±0.1).

EXAMPLE 7

The OSC is measured on the sample prepared according to Example 2, precipitated in the presence of an EO-surfactant. The result is about 2.4 ml $O_2$/g of mixed oxide (±0.1). The addition of surfactant had a significant effect on the OSC increase.

EXAMPLE 8

A pure cerium dioxide is prepared by adding ammonia to a solution of Ce nitrate in order to reach a pH value of about 9.0. The precipitated hydroxide is filtered on a Buchner filter and washed with about 12.5 ml of deionized water per gram of oxide. The surface area measured after calcination under air at about 900° C. for about 6 hours is about 2 $m^2/g$.

EXAMPLE 9

Example 8 is repeated. However, the precipitation is carried out in the presence of a Alkamide LE® surfactant. The concentration of surfactant in the Ce nitrate solution is about 2 weight percent. The surface area measured after calcination at about 900° C. for about 6 hours is about 4 $m^2/g$. This demonstrates the improvement of the thermal stability of pure ceria by using a surfactant in the process.

EXAMPLE 10

A co-thermohydrolysis procedure as described above is performed. This example illustrates the preparation of a cerium-zirconium mixed oxide ($Ce_{0.75}Zr_{0.25}O_2$). Combine a solution of ceric nitrate and zirconyl nitrate in the stoichiometric proportions required to obtain the desired composition. The nitrate solution is preneutralized with $NH_4OH$ to diminish the acidity. The concentration of the mixture (expressed in oxides of the different elements) is adjusted to about 80 g/l. The mixture is heated in an autoclave reactor at about 150° C. for about 4 hours. For the pulp which is obtained in this way, add about 27 g of Alkamide LE® surfactant. An ammonia solution is added to the previously described mixture until the pH is greater than about 8.5. The reaction mixture is heated to boiling for about 2 hours. After decanting the liquid from the solid, the resulting solid is resuspended and heated at about 100° C. for about 1 hour. The product is then filtered and calcined at about 600° C. for about 2 hours. The surface area is measured at about 32 m$^2$/g after calcination under air at about 900° C. for about 6 hours. Without the additive, the surface area is measured at about 19 m$^2$/g after calcination under air at about 900° C. for about 6 hours.

EXAMPLE 11

Utilizing a Mercury porosimeter supplied by Micromeritics samples of $CeO_2/ZrO_2$ 80/20% wt. mixed oxides prepared by coprecipitation are evaluated for pore volume (measured after calcination under air at about 500° C. for about two hours):

Sample A: prepared according to the coprecipitation method of Example 1 without surfactant additive achieves a total pore volume ml/g of about 0.35.

Sample B: prepared in accordance with Example 3 by addition of a nonionic surfactant, ALKAMIDE LE® surfactant (Lauramide DEA) supplied by Rhône-Poulenc Inc., achieves a total pore volume ml/g of about 0.88.

Sample C: prepared in accordance with Example 2 by addition of a nonionic surfactant, IGEPAL® CA-720 surfactant (Octyl Phenol Aromatic Ethoxylate) supplied by Rhône-Poulenc Inc., achieves a total pore volume ml/g of about 0.72.

EXAMPLE 12

Using a coprecipitation method, a nitrate solution of cerium and zirconium is added to an aqueous solution containing ammonia and lauric acid, to prepare a mixed oxide of composition: 80 wt % $CeO_2$ and 20 wt % $ZrO_2$. By reacting the various salts in stoichiometric amounts and adding to an ammonia solution which contains lauric acid, the hydroxides, corresponding to 22.5 g of dried rare earth oxides (REO) are precipitated out from the solution and filtered on a Büchner funnel. The ratio moles of lauric acid/moles of total metal is 0.2. The lauric acid is added only to the ammonia solution. The obtained wet cake is washed with 12.5 ml of deionized water per g of oxide and calcined under air for about 2 hours at about 500° C. The thermal stability of the product is evaluated after calcination under air in a muffle furnace at about 900° C. for about 6 hours. The surface area is measured at about 34 m$^2$/g by the B.E.T. method (Micromeritics Gemini 2360). The increase is about 49.0% compared to the product made without lauric acid. Lauric acid can be represented by the formula: $CH_3(CH_2)_{10}C(O)OH$

EXAMPLE 13

The thermal stability is measured for two samples, by measuring the surface area by the B.E.T. method (Micromeritics Gemini 2360 Norcross, Ga.) of three samples which are aged (under air) for about 6 hours at about 900° C., about 1000° C., and about 1100° C. The curves are shown below in FIG. 1.

Figure 1:
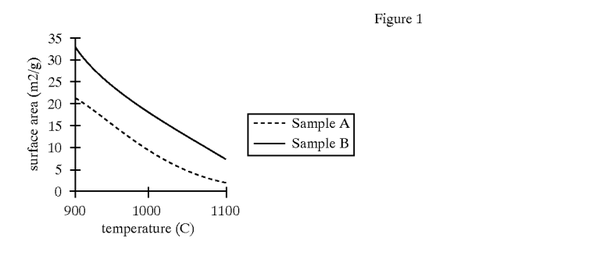

Sample A: prepared according to the coprecipitation method of Example 1 without additive.

Sample B: prepared according to Example 2 by the addition of a nonionic surfactant, IGEPAL® CA-720 surfactant (Octyl Phenol Aromatic Ethoxylate) supplied by Rhône-Poulenc Inc.

Figure 1

What is claimed is:

1. A process comprising the reaction of a Metal salt solution selected from the group consisting of a cerium solution, a zirconium solution, a cerium and zirconium solution and mixtures thereof, a base, optionally an oxidizing agent and an additive selected from the group consisting of:
   a) anionic surfactants;
   b) nonionic surfactants
   c) polyethylene glycols;
   d) carboxylic acids; and
   e) carboxylate salts;
   to form a product.

2. The process of claim 1 further comprising the step of washing or impregnating said product with an alkoxylated compound and/or an additive selected from the group consisting of:
   a) anionic surfactants;
   b) carboxylic acids; and
   c) carboxylate salts.

3. The process according to claim 1 wherein the reaction is an aqueous precipitation or coprecipitation.

4. The process according to claim 1 wherein the reaction is co-thermohydrolysis.

5. The process according to claim 1 wherein the nonionic surfactants are represented by the formula:

$$R_1-((CH_2)_x-O)_n-R_2$$

wherein $R_1$ and $R_2$ represent a linear or non-linear alkyl, aryl, and/or alkylaryl group or H or OH or Cl or Br or I; n is a number between about 1 and about 100; x is a number from about 1 to about 4 and $R_1$ and $R_2$ can contain an alcohol group, a CO group, or a S—C group.

6. The process according to claim 5 wherein the nonionic surfactant comprises a methoxy, ethoxy or propoxy group.

7. The process according to claim 1 wherein the anionic surfactants are selected from the group consisting of carboxylates, phosphates, sulfates, sulfonates and mixtures thereof.

8. The process according to claim 7 wherein the nonionic surfactants are selected from the group consisting of:
   acetylenic surfactants, alcohol ethoxylates, alkanolamides, amine oxides, ethoxylated alkanolamides, ethoxylated long chain amines, ethylene oxide/propylene oxide (EO/PO) co-polymers, sorbitan derivatives; ethylene glycol, propylene glycol, glycerol and polyglyceryl esters plus their ethoxylated derivatives; alkyl amines; alkyl imidazolines; ethoxylated oils and fats; alkyl phenol derivatives; and mixtures thereof.

9. The process according to claim 7, wherein the anionic surfactants are selected from the group consisting of:
   (a) ethoxycarboxylates having a moiety of the formula R—O—$(CH_2CH_2O)_xCH_xCOO^-$ where R is an alkyl or alkylaryl group, x is an integer from about to about 13;
   (b) ester carboxylates of the formula $R_1$—$CH_2$—$C(C(O)O^-)(OH)(-R_2)$, where $R_1$ is an alkyl or arylalkyl group, and R is an alkyl or arylalkyl group;
   (c) sarcosinates of the formula R—$C(O)N(CH_3)CH_2COO^-$, where R is an alkyl or arylalkyl group;
   (d) phosphate esters of the formula $R_2PO_4^-$, where R is an alkyl or allylaryl group;
   (e) sulfates of the formula $ROSO_3^-$, where R is an alkyl or alkylaryl group; and
   (f) sulfonates of the formula $RSO_3^-$, where R is an alkyl or alkylaryl group.

10. The process according to claim 7, wherein the anionic surfactants are selected from the group consisting of where $M^+$ is ammonium, potassium, sodium or triethanolammonium, and n is from about 1 to about 13, where R is an alkyl or alkylaryl group, n is independently the number of —$(CH_2CH_2O)$— moieties and M is hydrogen, sodium, potassium, or ammonium.

11. The process according to claim 7, wherein the anionic surfactants comprise a sulfate selected from the group consisting of alcohol sulfates, alcohol ether sulfates, and sulfated alkanolamide ethoxylates.

12. The process according to claim 7, wherein the anionic surfactants comprise a sulfonate selected from the group consisting of sulphosuccinates, taurates, isothionates, alkyl benzene sulfonates, fatty acid and diester sulfonates, α-sulfo fatty acid esters, alkyl naphthalene sulfonates, formaldehyde naphthalene sulfonates, olefin sulfonates, and petroleum sulphonates.

13. The process according to claim 7, wherein the anionic surfactants are selected from the group consisting of:

wherein R is an alkyl or alkyl group, Q is a propylene oxide moiety, n is independently the number of propylene oxide moieties and M is hydrogen, sodium, potassium, or ammonium.

14. The process of claim 1 wherein the nonionic surfactants and polyethylene glycols are added to the Metal salt solution, base or both before reaction.

15. The process of claim 1 wherein the carboxylic acids are added to the base before reaction.

16. The process according to claim 1 wherein the nonionic surfactants are ethoxylated tallowamines.

17. The process according to claim 1, wherein the nonionic surfactants are selected from the group consisting of:
   (a) octyl phenols having about 12 EO groups where EO is defined as —$CH_2CH_2O$)—;
   (b) nonylphenol ethoxylated polyethylene glycols having about 9 EO groups,
   (c) nonylphenols having about 5 to about 14 EO groups;
   (d) tristyrylphenol ethoxylates;
   (e) glycol mono ethers;
   (f) alkanolamides; and
   (g) lauryl dimethylamine oxide.

18. The process according to claim 17, wherein the nonionic surfactants are selected from the group consisting of:

19. The process of claim 11 wherein the reagents comprise an oxidizing agent and wherein the alkanolamides are added to the Metal salt solution, oxidizing agent or any combination thereof before the reaction.

20. A process comprising the step of washing or impregnating cerium hydroxides, cerium oxides, cerium hydroxy carbonates, cerium carbonates, zirconium hydroxides, zirconium oxides, zirconium hydroxy carbonates, zirconium carbonates, cerium/zirconium mixed hydroxides, cerium/zirconium mixed oxides, cerium/zirconium mixed hydroxy carbonates, cerium/zirconium mixed carbonates, cerium/zirconium hydroxide solid solutions, cerium/zirconium oxide solid solutions, cerium/zirconium hydroxy carbonate solid solutions cerium/zirconium carbonate solid solutions; and mixtures thereof with an additive selected from the group consisting of: anionic surfactants; carboxylic acids; carboxylate salts and mixtures thereof.

21. The process according to claim 20 wherein the additive is selected from the group consisting of carboxylic acids, carboxylate salts and mixtures thereof.

22. The process according to claim 21 wherein the additive is a carboxylic acid.

23. The process according to claim 20, wherein the anionic surfactants are selected from the group consisting of:
   (a) ethoxycarboxylates having a moiety of the formula R—O—$(CH_2CH_2O)_xCH_2COO^-$ where R is an alkyl or alkylaryl group, wherein x is an integer from about 1 to about 13;
   (b) ester carboxylates of the formula $R_1$—$CH_2$—$C(C(O)O^-)(OH)(-R_2)$, where $R_1$ is an alkyl or arylalkyl group, and $R_2$ is an alkyl or arylalkyl group;
   (c) sarcosinates of the formula R—$C(O)N(CH_3)CH_2COO^-$, where R is an alkyl or arylalkyl group;
   (d) phosphate esters of the formula $R_2PO_4^-$; where R is an alky or alkylaryl group;
   (e) sulfates of the formula $ROSO_3^-$, where R is an alkyl or alkylaryl group; and
   (f) sulfonates of the formula $RSO_3^-$, where R is an allyl or alkylaryl group.

24. The process according to claim 20, wherein the anionic surfactants are selected from the group consisting of:

where M$^+$ is ammonium, potassium, sodium or triethanolammonium, and n is from about 1 to about 13, where R is an alkyl or alkylaryl group, n is independently the number of —(CH$_2$CH$_2$O)— moieties and M is hydrogen, sodium, potassium, or ammonium.

25. The process according to claim 20, wherein the anionic surfactants comprise a sulfate selected from the group consisting of alcohol sulfates, alcohol ether sulfates, and sulfated alkanolamide ethoxylates.

26. The process according to claim 20, wherein the anionic surfactants comprise a sulfonate selected from the group consisting of sulphosuccinates, taurates, isothionates, alkyl benzene sulfonates, fatty acid and diester sulfonates, α-sulfo fatty acid esters, alkyl naphthalene sulfonates, formaldehyde naphthalene sulfonates, olefin sulfonates, and petroleum sulphonates.

27. The process according to claim 20, wherein the anionic surfactants are selected from the group consisting of:

wherein R is an alkyl or allylaryl group, Q is a propylene oxide moiety, n is independently the number of propylene oxide moieties and M is hydrogen, sodium, potassium, or ammonium.

28. A process comprising the step of washing or impregnating cerium hydroxides, cerium oxides, cerium hydroxy carbonates, cerium carbonates, zirconium hydroxides, zirconium oxides, zirconium hydroxy carbonates, zirconium carbonates, cerium/zirconium mixed hydroxides, cerium/zirconium mixed oxides, cerium/zirconium mixed hydroxy carbonates, cerium/zirconium mixed carbonates, and mixtures thereof with an additive selected from the group consisting of anionic surfactants, carboxylic acids, carboxylic salts and mixtures thereof.

29. The process according to claim 28 wherein the additive is selected from the group consisting of carboxylic acids, carboxylate salts and mixtures thereof.

30. The process according to claim 29 wherein the additive is a carboxylic acid.

31. The process according to claim 28, wherein the anionic surfactants are selected from the group consisting of:

where M$^+$ is ammonium, potassium, sodium or triethanolammonium, and n is from about 1 to about 13, where R is an alkyl or alkylaryl group, n is independently the number of —(CH$_2$CH$_2$O)— moieties and M is hydrogen, sodium, potassium, or ammonium.

32. The process according to claim 28, wherein the anionic surfactants comprise a sulfate selected from the group consisting of alcohol sulfates, alcohol ether sulfates, and sulfated alkanolamide ethoxylates.

33. The process according to claim 28, wherein the anionic surfactants comprise a sulfonate selected from the group consisting of sulphosuccinates, taurates, isothionates, alkyl benzene sulfonates, fatty acid and diester sulfonates, α-sulfo fatty acid esters, alkyl naphthalene sulfonates, formaldehyde naphthalene sulfonates, olefin sulfonates, and petroleum sulphonates.

34. The process according to claim 28, wherein the anionic surfactants are selected from the group consisting of:

wherein R is an alkyl or alkylaryl group, Q is a propylene oxide moiety, n is independently the number of propylene oxide moieties and M is hydrogen, sodium, potassium, or ammonium.

35. The process according to claim 28, wherein the anionic surfactants are selected from the group consisting of:
(a) ethoxycarboxylates having a moiety of the formula R—O—(CH$_2$CH$_2$O)$_x$CH$_2$COO$^-$ where R is an alkyl or alkylaryl group, wherein x is an integer from about 1 to about 13;
(b) ester carboxylates of the formula: R$_1$—CH$_2$—C(C(O)O$^-$)(OH)(—R$_2$), where R$_1$ is an alkyl or arylalkyl group, and R$_2$ is an alkyl or arylalkyl group;
(c) sarcosinates of the formula R—C(O)N(CH$_3$)CH$_2$COO$^-$, where R is an alkyl or arylalkyl group;
(d) phosphate esters of the formula R$_2$PO$_4^-$, where R is an alkyl or alkylaryl group;
(e) sulfites of the formula ROSO$_3^-$, where R is an alkyl or alkylaryl group; and
(f) sulfonates of the formula RSO$_3^-$, where R is an alkyl or alkylaryl group.

* * * * *